United States Patent
Hsu et al.

(10) Patent No.: US 8,703,060 B2
(45) Date of Patent: Apr. 22, 2014

(54) APPARATUS FOR TESTING CATALYST

(75) Inventors: Ning-Yih Hsu, Keelung (TW); Chun Ching Chien, Taipei (TW); Chao Yu, Taoyuan County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 288 days.

(21) Appl. No.: 13/175,914

(22) Filed: Jul. 4, 2011

(65) Prior Publication Data
US 2013/0011299 A1      Jan. 10, 2013

(51) Int. Cl.
| | |
|---|---|
| G01N 31/12 | (2006.01) |
| G01N 7/00 | (2006.01) |
| G01N 21/00 | (2006.01) |
| G01N 27/00 | (2006.01) |
| G01N 31/00 | (2006.01) |
| G01N 33/00 | (2006.01) |
| B01J 10/00 | (2006.01) |
| B01J 10/02 | (2006.01) |
| B01J 12/00 | (2006.01) |
| B01J 12/02 | (2006.01) |
| B01J 14/00 | (2006.01) |
| B01J 15/00 | (2006.01) |
| B01J 16/00 | (2006.01) |
| B01J 19/00 | (2006.01) |

(52) U.S. Cl.
USPC .............................................. 422/78; 83/129

(58) Field of Classification Search
CPC .................................. B01J 9/00; B01J 9/0093
USPC ............................................... 422/78, 83, 129
See application file for complete search history.

(56) References Cited

U.S. PATENT DOCUMENTS

| | | | | |
|---|---|---|---|---|
| 3,002,583 | A * | 10/1961 | Findlay | 95/12 |
| 4,333,735 | A * | 6/1982 | Hardy et al. | 436/114 |
| 5,051,395 | A * | 9/1991 | Mitchell et al. | 502/348 |
| 6,306,349 | B1 * | 10/2001 | Moon et al. | 422/69 |
| 7,288,231 | B2 * | 10/2007 | Tonkovich et al. | 422/177 |
| 7,306,770 | B2 * | 12/2007 | Bauman et al. | 422/129 |
| 2007/0161758 | A1 * | 7/2007 | Sultan et al. | 525/342 |

* cited by examiner

*Primary Examiner* — Sam P Siefke
*Assistant Examiner* — Bryan Kilpatrick
(74) *Attorney, Agent, or Firm* — Jackson IPG PLLC

(57) ABSTRACT

A catalyst-testing apparatus includes a heater, a U-shaped reactor, a gas flow controller, a liquid flow controller, two pressure gauges, a separator and a chromatograph. In use, under control of the gas flow controller, natural gas and air are directed to the U-shaped reactor. Under control of the liquid flow controller, pure water is directed to the U-shaped reactor. The pure water travels down the wall of the U-shaped reactor. The pure water is heated and turned into steam in a front section of the U-shaped reactor. Together with the natural gas and the air, the steam is directed to a catalyst zone in the U-shaped reactor for reaction. With the chromatograph, volumes and compositions of resultant gases are analyzed. Thus, the stability of the performance of the catalyst is tested, and the performance of the catalyst for producing hydrogen by is revealed.

11 Claims, 1 Drawing Sheet

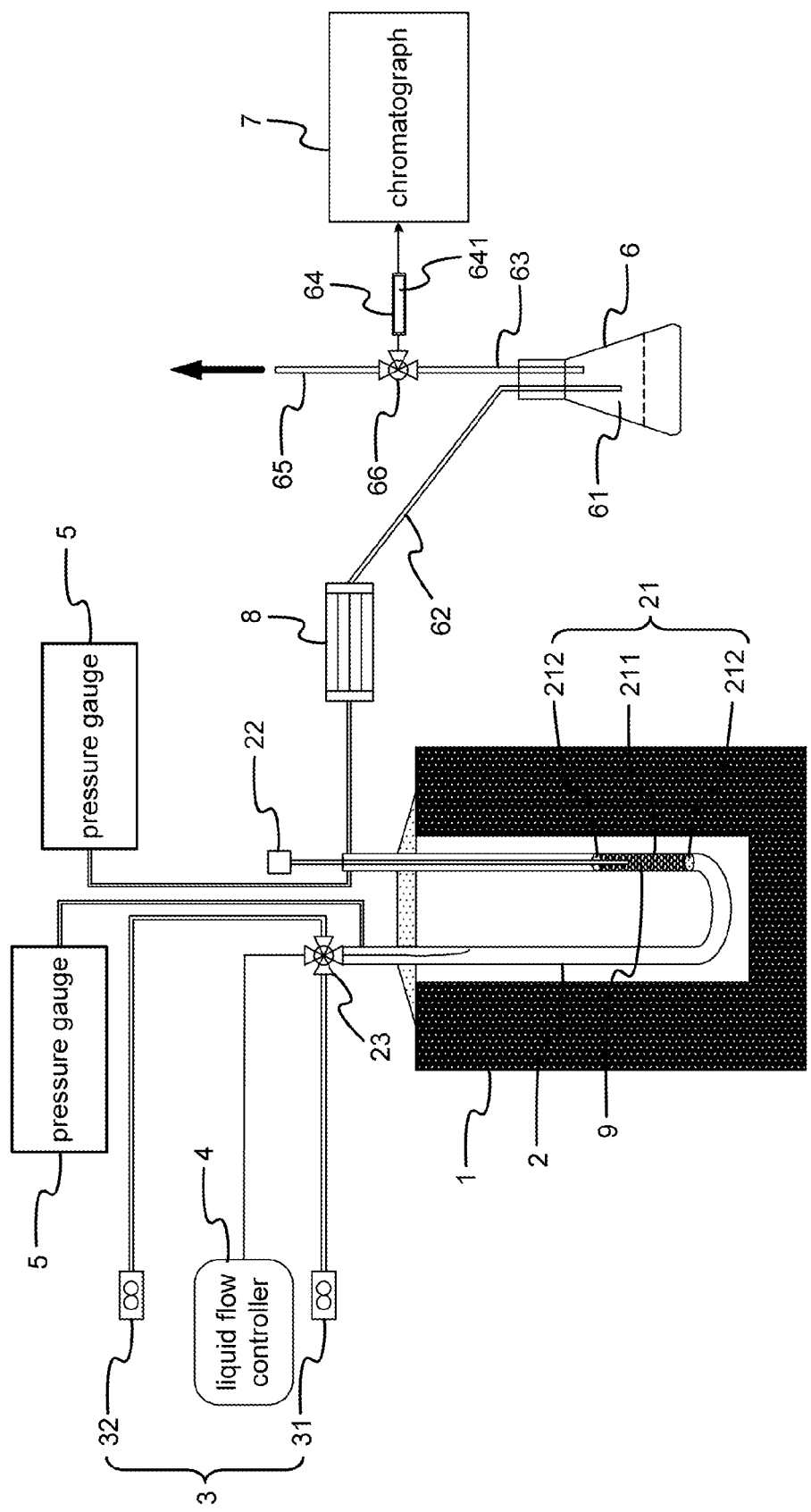

APPARATUS FOR TESTING CATALYST

BACKGROUND OF INVENTION

1. Field of Invention

The present invention relates to catalyst and, more particularly, to an apparatus for testing catalyst.

2. Related Prior Art

Since the industrial revolution in the eighteenth century, people have been using machines that consume large amounts of energy. Fossil fuels have energized the development of human societies. The use of the fossil fuel has however entailed global warming. As attempts to reduce the global warming, there have been exploited various energy sources such as solar energy, wind energy, bio-fuels and hydrogen. The density of the solar energy is low, and the production of solar cells for using the solar energy is not environmentally friendly. The stability of the wind energy is poor. The bio-fuels compete against food regarding the raw materials. Hydrogen seems to be the most promising energy source among these energy sources for several reasons. At first, hydrogen exhibits a high energy density compared with the solar energy. Secondly, hydrogen excellent stability compared with the wind energy. Thirdly, hydrogen does not entail food shortage like the bio-fuels.

The production of hydrogen is important. The resultant hydrogen can be used in various fuel cells among which solid oxide fuel cells seem to be the most important. Hydrogen can be made of methane, methanol, ethanol, natural gas, liquefied petroleum gas ("LPG") and gasoline for example. These raw materials can be recombined at high temperatures to produce hydrogen. Catalysts are an important factor for the production of hydrogen. With excellent catalysts and proper operative conditions, high yields (Y %) of hydrogen and high conversion rates (X %) of hydrogen are achieved.

Hence, it is important to test the performance of the catalysts. There have been various apparatuses for testing the catalysts. These conventional catalyst-testing apparatuses however only accept gaseous raw materials. As a raw material, water has to be heated and turned into steam before it can be introduced into a conventional catalyst-testing apparatus, mixed with natural gas and air, and turned into a reformate by a catalyst. It is inconvenient to use an independent heater to heat and turn the water into the steam and then introduce the steam into the conventional apparatus.

The present invention is therefore intended to obviate or at least alleviate the problems encountered in prior art.

SUMMARY OF INVENTION

It is the primary objective of the present invention to provide a convenient apparatus for testing catalysts.

To achieve the foregoing objective, the catalyst-testing apparatus includes a tubular heater, a U-shaped reactor, a thermocouple, a gaseous mass flow controlling assembly, a liquid flow controller, two pressure gauges, a cooler, a separator and a chromatograph. The tubular heater is used for vaporizing water, preheating gas and controlling the temperature for reaction. The tubular heater is made with an internal diameter of 52 to 78 mm and a length of 160 to 240 mm. The U-shaped reactor includes an inlet, an outlet and a catalyst zone located between the inlet and the outlet for receiving catalyst. The U-shaped reactor is located in the tubular heater except the inlet and the outlet. The U-shaped reactor is made with an internal diameter of 8 to 12 mm, an external diameter of 9.6 to 14.4 mm and a length of 720 to 1080 mm. The thermocouple is connected to the catalyst zone via the outlet of the U-shaped reactor. The gaseous mass flow controlling assembly is connected to the inlet of the U-shaped reactor for feeding natural gas and air into the U-shaped reactor in a quantitative manner. The liquid flow controller is connected to the inlet of the U-shaped reactor for feeding water into the U-shaped reactor in a quantitative manner so that the water travels down an internal side of the U-shaped reactor and gets heated and turned into steam during the travel so that the steam, the natural gas and the air react with one another. The pressure gauges are respectively connected to the inlet and outlet of the U-shaped reactor for measuring pressure difference between the inlet and outlet of the U-shaped reactor to determine whether there is efflorescence of the catalyst or precipitation of carbon from the catalyst that would stick to the internal side of the U-shaped reactor and cause the pressure to increase in the U-shaped reactor. The cooler is connected to the outlet of the U-shaped reactor for cooling and condensing resultant gas from the U-shaped reactor. The separator is connected to the cooler. Liquid is separated from gas and the gas is dried in the separator. The chromatograph is connected to the separator. The gas is analyzed to reveal the composition of the gas.

The tubular heater may be a programmable high-temperature oven.

The internal diameter of the tubular heater may be 65 mm and the length of the tubular heater may be 200 mm.

The U-shaped reactor may be a U-shaped pipe made of quartz.

The internal diameter of the U-shaped reactor is 10 mm, the external diameter of the U-shaped reactor is 12 mm, and the length of the U-shaped reactor is 900 mm.

The gaseous mass flow controlling assembly may include a gas flow controller and an air flow controller.

The catalyst-testing apparatus may further include a four-pass pipe made with a section connected to the inlet of the U-shaped reactor, another section connected to the air flow controller, another section connected to the gas flow controller and another section connected to the liquid flow controller.

The liquid flow controller may be a syringe pump.

The catalyst-testing apparatus may further include a pipe for connecting the cooler to the separator.

The catalyst-testing apparatus may further include a primary pipe for connecting the separator to the chromatograph.

The catalyst-testing apparatus may further include a polyethylene pipe, an exhaust pipe and a three-pass pipe including a section connected to the primary pipe, another section connected to the polyethylene pipe and another section connected to the exhaust pipe.

The catalyst-testing apparatus may further include a drying agent located in the polyethylene pipe.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawing wherein:

FIG. 1 is a perspective view of a catalyst-testing apparatus according to the preferred embodiment of the present invention.

DETAILED DESCRIPTION OF PREFERRED EMBODIMENT

Referring to FIG. 1, there is shown a catalyst-testing apparatus according to the preferred embodiment of the present invention. The catalyst-testing apparatus includes a tubular heater 1, a U-shaped reactor 2, a gaseous mass flow controlling assembly 3, a liquid flow controller 4, two pressure gauges 5, a separator 6, a chromatograph 7 and a cooler 8.

The tubular heater 1 is preferably a programmable high-temperature oven that can operate at 1000 degrees Celsius. The tubular heater 1 is used to vaporize water, preheat gases and control the temperature for reaction. The internal diameter of the tubular heater 1 is 52 to 70 mm and preferably 65 mm. The length of the tubular heater 1 is 160 to 240 mm and preferably 200 mm.

The U-shaped reactor 2 is a U-shaped pipe made of quartz and formed with an inlet and an outlet. The internal diameter of the U-shaped reactor 2 is 8 to 12 mm and preferably 10 mm. The external diameter of the U-shaped reactor 2 is 9.6 to 14.4 mm and preferably 12 mm. The length of the U-shaped reactor 2 is 720 to 1080 mm and preferably 900 mm.

There is a catalyst zone 21 located in the U-shaped reactor 2. The catalyst zone 21 is filled with catalyst 9. Preferably, the catalyst zone 21 includes a quartz pipe 211 located between two round masses of quartz filaments 212. The diameter of the quartz pipe 211 is 3 mm and the length of the quartz pipe 211 is 3 cm. The weight of the catalyst 9 is 7 grams.

The U-shaped reactor 2 is located in the tubular heater 1 except the inlet and outlet. A thermocouple 22 is substantially located outside the U-shaped reactor 2. The thermocouple 22 however includes a portion inserted into the catalyst zone 21 of the U-shaped reactor 2 through the outlet of the U-shaped reactor 2 so that the temperature of the catalyst 9 can be measured by the thermocouple 22.

A four-pass pipe (or "cross pipe") 23 includes four sections. The first section of the four-pass pipe 23 is connected to the inlet of the U-shaped reactor 2.

The gaseous mass flow controlling assembly 3 includes an air flow controller 31 connected to the second section of the four-pass pipe 23 and a gas flow controller 32 connected to the third section of the four-pass pipe 23. The air flow controller 31 is used to feed air into the U-shaped reactor 2 in a quantitative manner. The gas flow controller 32 is used to feed natural gas into the U-shaped reactor 2 in a quantitative manner.

The liquid flow controller 4 is preferably a syringe pump connected to the fourth section of the four-pass pipe 23. In a quantitative manner, the liquid flow controller 4 feeds water into the U-shaped reactor 2 through a stainless steel pipe made with a diameter of 1/16 (one sixteenth) inch.

One of the pressure gauges 5 is connected to the inlet of the U-shaped reactor 2 while the other pressure gauge 5 is connected to the outlet of the U-shaped reactor 2. The pressure gauges 5 measure the pressure difference between the inlet and outlet of the U-shaped reactor 2 and determine whether there is efflorescence of the catalyst 9 or precipitation of carbon from the catalyst 9 that would stick to the internal side of the U-shaped reactor 2 and cause the pressure to increase in the U-shaped reactor 2.

The separator 6 is located near the outlet of the U-shaped reactor 2. The separator 6 includes a space 61 defined therein, two pipes 62 and 63, a polyethylene ("PE") pipe 64, an exhaust pipe 65 and a three-pass pipe 66. Each of the pipes 62 and 63 includes a section located outside the space 61 and another section inserted in the space 61. The three-pass pipe 66 includes three sections. The first section of the three-pass pipe 66 is connected to the pipe 63. The second section of the three-pass pipe 66 is connected to the PE pipe 64. The third section of the three-bass pipe 66 is connected to exhaust pipe 65.

The cooler 8 is provided between the separator 6 and the outlet of the U-shaped reactor 2. In specific, the cooler 8 is connected to the separator 6 through the pipe 62 and connected to the outlet of the U-shaped reactor 2 via another pipe. The cooler 8 cools and condenses resultant gas from the U-shaped reactor 2 so that gas is separated from liquid. The liquid is sent to the space 61 defined in the separator 6. The gas is directed through the polyethylene ("PE") pipe 64. A drying agent 641 is filled in the PE pipe 64 to dry the gas to be introduced into the chromatograph 7. If there is excessive gas, some of it is released through the exhaust pipe 65.

The chromatograph 7 is connected to the separator 6. The separated and dried gas is sent from the separator 6 into the chromatograph 7 in which the gas is analyzed to reveal the composition of the gas.

In use, the natural gas and the air are fed into the U-shaped reactor 2 in a quantitative manner by the gaseous mass flow controlling assembly 3. The water is fed into the U-shaped reactor 2 by the liquid flow controller 4. The water travels down the internal side of the U-shaped reactor 2. During the travel, the water gets heated and turned into steam. The steam, the natural gas and the air react with one another and are recombined in the catalyst zone 21. The reaction lasts for about 3 minutes. The resultant hot gas is cooled and condensed by the cooler 8. Then, liquid is separated from gas by the separator 6. The gas is fed into the chromatograph 7 in which the gas is analyzed. Every hour, the composition of the gas is analyzed and recorded. The pressure gauges 5 are respectively connected to the inlet of the U-shaped reactor 2 while the other pressure gauge 5 is connected to the outlet of the U-shaped reactor 2. The pressure gauges 5 measure the pressure difference between the inlet and outlet of the U-shaped reactor 2 and determine whether there is efflorescence of the catalyst 9 or precipitation of carbon from the catalyst 9 that would stick to the internal side of the U-shaped reactor 2 and cause the pressure to increase in the U-shaped reactor 2.

Advantageously, the water, the natural gas and the air are synchronously fed into the U-shaped reactor 2. The water does not have to be heated and turned into the steam before it is fed into the U-shaped reactor 2. The structure of the catalyst-testing apparatus is simple, the operation of the catalyst-testing apparatus is smooth, and the costs of the purchase and use of the catalyst-testing apparatus are low.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:
1. A catalyst-testing apparatus including:
a tubular heater 1 for vaporizing water, preheating gas and controlling the temperature for reaction, wherein the tubular heater 1 is made with an internal diameter of 52 to 78 mm and a length of 160 to 240 mm;
a U-shaped reactor 2 made of quartz including an inlet, an outlet and a catalyst zone 21 located between the inlet and the outlet and comprising a quartz pipe located between two round masses of quartz filaments and configured for receiving catalyst 9, wherein the U-shaped reactor 2 is located in the tubular heater 1 except the inlet and the outlet, wherein the U-shaped reactor 2 is made with an internal diameter of 8 to 12 mm, an external diameter of 9.6 to 14.4 mm and a length of 720 to 1080 mm;

a thermocouple 22 connected to the catalyst zone 21 through the outlet of the U-shaped reactor 2;

a gaseous mass flow controlling assembly 3 connected to the inlet of the U-shaped reactor 2 for feeding natural gas and air into the U-shaped reactor 2 in a quantitative manner;

a liquid flow controller 4 connected to the inlet of the U-shaped reactor 2 for feeding liquid water into the U-shaped reactor 2 in a quantitative manner so that the liquid water travels down an internal side of the U-shaped reactor 2 and gets heated and turned into steam during the travel so that the steam, the natural gas and the air react with one another;

two pressure gauges 5 respectively connected to the inlet and outlet of the U-shaped reactor 2 for measuring pressure difference between the inlet and outlet of the U-shaped reactor 2 to determine whether there is efflorescence of the catalyst 9 or precipitation of carbon from the catalyst 9 that would stick to the internal side of the U-shaped reactor 2 and cause the pressure to increase in the U-shaped reactor 2;

a cooler 8 connected to the outlet of the U-shaped reactor 2 for cooling and condensing resultant gas from the U-shaped reactor 2;

a separator 6 connected to the cooler 8, wherein liquid is separated from gas and the gas is dried in the separator 6; and a chromatograph 7 connected to the separator 6, wherein the gas is analyzed to reveal the composition of the gas.

2. The catalyst-testing apparatus according to claim 1, wherein the tubular heater 1 is a programmable high-temperature oven, wherein the internal diameter of the tubular heater 1 is 65 mm and the length of the tubular heater 1 is 200 mm.

3. The catalyst-testing apparatus according to claim 1, wherein the U-shaped reactor 2 is a U-shaped pipe, wherein the internal diameter of the U-shaped reactor 2 is 10 mm, the external diameter of the U-shaped reactor 2 is 12 mm, and the length of the U-shaped reactor 2 is 900 mm.

4. The catalyst-testing apparatus according to claim 1, wherein the gaseous mass flow controlling assembly 3 includes a gas flow controller 31 and an air flow controller 32.

5. The catalyst-testing apparatus according to claim 4, further including a four-pass pipe 23 including a section connected to the inlet of the U-shaped reactor 2, another section connected to the air flow controller 31, another section connected to the gas flow controller 32 and another section connected to the liquid flow controller 4.

6. The catalyst-testing apparatus according to claim 1, wherein the liquid flow controller 4 is a syringe pump.

7. The catalyst-testing apparatus according to claim 1, further including a three-pass pipe 23 including a section connected to the inlet of the U-shaped reactor 2, another section connected to the gaseous mass flow controlling assembly 3, and another section connected to the liquid flow controller 4.

8. The catalyst-testing apparatus according to claim 1, further including a pipe 62 for connecting the cooler 8 to the separator 6.

9. The catalyst-testing apparatus according to claim 1, further including a primary pipe 63 for connecting the separator 6 to the chromatograph 7.

10. The catalyst-testing apparatus according to claim 9, further including:
a polyethylene pipe 64;
an exhaust pipe 65; and
a three-pass pipe 66 including a section connected to the primary pipe 63, another section connected to the polyethylene pipe 64 and another section connected to the exhaust pipe 65.

11. The catalyst-testing apparatus according to claim 10, further including a drying agent 641 located in the polyethylene pipe 64.

* * * * *